United States Patent [19]

Rendenbach-Mueller et al.

[11] Patent Number: 5,418,235
[45] Date of Patent: May 23, 1995

[54] AMINOALKYL-SUBSTITUTED 5-MERCAPTOTHIAZOLES, THE PREPARATION AND USE THEREOF

[75] Inventors: Beatrice Rendenbach-Mueller, Waldsee; Liliane Unger, Ludwigshafen; Hans-Juergen Teschendorf, Dudenhofen, all of Germany

[73] Assignee: BASF Aktiengesellschaft, Ludwigshafen, Germany

[21] Appl. No.: 162,145

[22] PCT Filed: May 8, 1992

[86] PCT No.: PCT/EP92/01004

§ 371 Date: Dec. 13, 1993

§ 102(e) Date: Dec. 13, 1993

[87] PCT Pub. No.: WO92/22540

PCT Pub. Date: Dec. 23, 1992

[30] Foreign Application Priority Data

Jun. 15, 1991 [DE] Germany ............... 41 19 756.9

[51] Int. Cl.6 ............... C07D 417/12; C07D 277/40; A61K 31/425; A61K 31/435
[52] U.S. Cl. .................. 514/252; 514/326; 514/342; 544/364; 544/369; 544/367; 546/204; 546/280; 548/184

[58] Field of Search ............ 548/184; 546/209; 544/364, 367; 514/252, 376, 342, 369

[56] References Cited

U.S. PATENT DOCUMENTS 3,717,651  2/1973  Pilgram et al. ............... 514/367
5,071,864  12/1991  Rendenbach-Mueller et al. ............... 514/370

FOREIGN PATENT DOCUMENTS 345533  12/1989  European Pat. Off. .
412404  2/1991  European Pat. Off. .

*Primary Examiner*—Robert Gerstl
*Attorney, Agent, or Firm*—Keil & Weinkauf

[57] ABSTRACT

Aminoalkyl-substituted 5-mercaptothiazoles of the formula

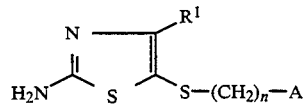

where $R^1$, n and A have the meanings stated in the description, and the preparation thereof are described.

The compounds are suitable for controlling diseases.

11 Claims, No Drawings

AMINOALKYL-SUBSTITUTED 5-MERCAPTOTHIAZOLES, THE PREPARATION AND USE THEREOF

This application is a 371/of PCT/EP92/01004 filed May 8, 1992.

The present invention relates to novel amino-alkyl-substituted 5-mercaptothiazoles, the preparation thereof and the use thereof for controlling diseases.

U.S. Pat. No. 3,717,651 describes, inter alia, 5-mercapto-substituted thiazoles which have herbicidal properties.

We have now found that aminoalkyl-substituted 5-mercaptothiazoles of the formula I

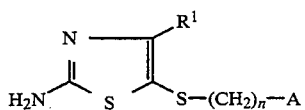

where
$R^1$ is H, $C_1$–$C_5$-alkyl, phenyl which is unsubstituted or substituted by halogen, $C_1$–$C_5$-alkyl or $C_1$–$C_5$-alkoxy, or is thienyl,
n is an integer from 2 to 6,
A is $NR^2R^3$ where $R^2$ and $R^3$, which can be identical or different, are each hydrogen, $C_1$–$C_5$-alkyl, which is unsubstituted or substituted by phenyl or thienyl, or is

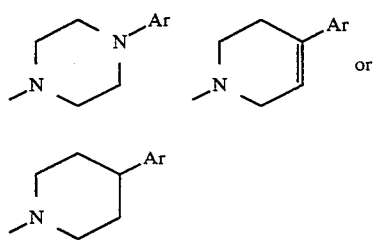

where Ar is phenyl which is unsubstituted or mono-substituted by $C_1$–$C_5$-alkyl, $C_1$–$C_5$-alkoxy, halogen, nitro, hydroxyl, trifluoromethyl or cyano, or is pyridyl, pyrimidinyl or thienyl,
and their salts with physiologically tolerated acids are very suitable for controlling diseases.

In the formula I, $R^1$ is preferably H or $C_1$–$C_5$-alkyl, A is preferably

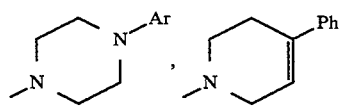

or $C_1$–$C_5$-alkyl $A_r$ is unsubstituted phenyl or phenyl monosubstituted by and n is preferably 2 or 3.

The compounds of the formula I can be prepared by
a) reacting a 5-mercaptothiazole of the formula II

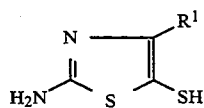

where $R^1$ is as defined above, or a salt of this compound, with an ω-X-alkylamine of the formula III $$X-(CH_2)_n-A \qquad III$$

where A and n are as defined above, and X is a leaving group such as chlorine, bromine or $R^4SO_2O$—[$R^4=C_1$–$C_4$-alkyl or phenyl which is unsubstituted or substituted by $C_1$–$C_3$-alkyl or halogen], or b) reacting an ω-alkyl-substituted 5-mercaptothiazole of the formula IV

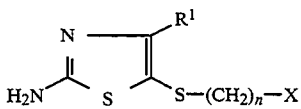

where $R^1$, n and X have the stated meanings, or a salt of this compound, with an amine of the formula V $$HA \qquad V$$

where A is as defined above, or
c) reacting an ω-mercaptoalkylamine of the formula VI $$HS-(CH_2)_n-A \qquad VI$$

where A and n are as defined above, with a 5-Y-substituted thiazole of the formula VII

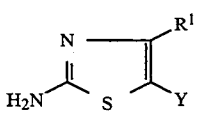

where $R^1$ is as defined above, and Y is chlorine or bromine, or with a hydrohalic acid salt of this compound,
and converting the resulting compounds where appropriate into their salts with physiologically tolerated acids.

The reactions in process a) preferably take place in a solvent at from room temperature to the boiling point of the solvent, where appropriate in the presence of an acid acceptor. Examples of solvents which can be used are dimethylformamide, or ketones such as acetone or butanone, and of acid acceptors are inorganic bases such as sodium or potassium carbonate or tertiary organic bases such as triethylamine or pyridine. In excess, the latter can also act as solvent.

The crude product is isolated in a conventional way, eg. by filtration, removal of the solvent by distillation, or extraction from the reaction mixture. The resulting compound is purified in a conventional way, for example by recrystallization from a solvent, chromatography or conversion into an acid addition compound.

The 5-mercaptothiazoles of the formula II used as starting materials are known from the literature or can be prepared by treating a thiazole of the formula VIII

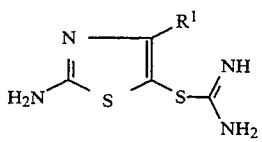

where $R^1$ is as defined above, or a hydrohalic acid salt of this compound, with bases such as aqueous ammonia solution or sodium hydroxide solution, if required also in a two-phase mixture. Another possibility for the synthesis comprises reacting the thiazoles of the formula VII with inorganic sulfides such as potassium hydrogen sulfide. The mercaptothiazoles of the formula II need not be isolated for subsequent reactions. Thus, for example, it is also possible to obtain the compounds of the formula I according to the invention by treating a mixture of the thiazoles of the formula VIII and of the ω-X-alkylamines of the formula III with a base, in which case the mercaptothiazole of the formula II which is formed in situ immediately reacts with the alkylamines of the formula III.

The reactions in process b) take place in the melt, if required also in the presence of a solvent such as ethyl acetate, tetrahydrofuran, dimethylformamide, dimethoxyethane, toluene or xylene, at from room temperature to the boiling point of the solvent, preferably in the presence of a base such as sodium methylate, sodium ethylate, sodium hydride, sodium carbonate, potassium carbonate, or of an amine such as pyridine. It is also possible where appropriate for the amine component IV in excess to act as reagent, base and solvent.

The reactions in process c) take place in a solvent at from room temperature to the boiling point of the solvent. Examples of suitable solvents are dimethylformamide, dimethoxyethane, tetrahydrofuran or a ketone such as acetone or butanone. It is beneficial to add a base such as sodium or potassium carbonate, sodium hydroxide, or a tertiary amine such as pyridine or triethylamine.

The thiazoles of the formula VII and mercaptoalkylamines of the formula VI which are used as starting materials can, where they are not known from the literature, be prepared by conventional methods.

The resulting compounds according to the invention are, where appropriate, converted into their addition salts with physiologically tolerated acids. Examples of suitable physiologically tolerated organic and inorganic acids are hydrochloric acid, hydrobromic acid, phosphoric acid, sulfuric acid, oxalic acid, maleic acid, fumaric acid, lactic acid, tartaric acid, adipic acid and benzoic acid. Others are to be found in Fortschritte der Arzneimittelforschung, Vol. 10, pp. 224 et seq., Birkhäuser Verlag, Basel and Stuttgart, 1966.

The acid addition salts are usually obtained in a conventional way by mixing the free base or solutions thereof with the appropriate acid or solutions thereof in an organic solvent, for example a lower alcohol such as methanol, ethanol or propanol, a halohydrocarbon such as methylene chloride, an ether such as methyl t-butyl ether or diisopropyl ether, a ketone such as acetone or butanone or an ester such as ethyl acetate. It is also possible to use mixtures of the said solvents to improve crystallization. In addition, pharmaceutically acceptable aqueous solutions of acid addition compounds of the compounds I according to the invention can be prepared by dissolving the free bases in an aqueous acid solution.

The compounds according to the invention are suitable for controlling diseases, especially for treating disorders of the central nervous system (eg. parkinsonism, schizophrenia) and high blood pressure. They have, in particular, valuable properties as dopamine receptors, in some cases with selectivity for presynaptic dopamine receptors, or as dopamine antagonists. The compounds of the formula I show affinity for the dopamine receptor in receptor binding assays; they inhibit motility in mice (measured in cages with a photoelectric beam) and influence the pivoting behavior of rats with unilateral 6-hydroxydopamine lesions of the substantia nigra (Brain Research 24, (1970) 485–493).

The effects of the novel compounds can be shown in the receptor binding assay as follows:

Striata from rats (Sprague Dawley, Charles River) were homogenized immediately after removal in 0.32M sucrose solution (0° C.). The homogenate was filtered through gauze, the filtrate was centrifuged at 1000 ×g (5 min at 4° C.) and the resulting supernatant was centrifuged at 40000 ×g (4° C., 10 min). The residue (membranes) was taken up in incubation buffer (50 mM tris-HCl, 1 mM $MgCl_2$ and 0.1% ascorbic acid, pH 7.4) and incubated at 37° C. for 20 min. The residue was subsequently washed 2× with incubation buffer by resuspension and recentrifugation. The membranes were frozen in portions in liquid nitrogen.

The assay mixtures (1 ml) were composed of membranes (380 µg of protein), 1 nM $^3$H-ADTN (NEN, Dreieich Germany, specific radioactivity 1.4 TBq/mmol) and 0.1 µM SCH 23390 (total binding) or a) with the addition of 50 nM spiperone (non-specific binding) or b) with test substance. The mixtures were prepared in triplicate.

After the incubation (40 min at 25° C.) the mixtures were filtered through glass fiber filters (Whatman GF/B) and briefly washed with ice-cold washing buffer (tris-HCl, pH 7.4). The radioactivity retained on the filters was determined by liquid scintillation counting. The non-specific binding comprised about 40–50% of the total binding.

The evaluation of the competition plots and the determination of the dissociation constant took place by iterative non-linear regression analysis based on the "ligand" program (Muson and Rodbard: Anal. Biochem. 107 (1980) 220).

Affinity of the test substances for the dopamine $D_2$ receptor

| Example | Ki (nM) |
|---------|---------|
| 1 | 12 |
| 2 | 3 |
| 3 | 19 |
| 5 | 18 |
| 7 | 9 |

The compounds according to the invention can be administered orally or parenterally ( subcutaneously, intravenously, intramuscularly, intraperitoneally ) in a conventional way. Administration can also take place through the nasopharyngeal space using vapors or sprays.

The dosage depends on the age, condition and weight of the patient and on the mode of administration. The dose of active substance is, as a rule, about 10–500 mg per patient and day on oral administration and about 1–100 mg per patient and day on parenteral administration.

The novel compounds can be used in the conventional solid or liquid pharmaceutical forms, eg. as uncoated or (film) coated tablets, capsules, powders, granules, suppositories, solutions or sprays. These are produced in a conventional way. The active substances can be processed with conventional pharmaceutical aids such as tablet binders, fillers, preservatives, tablet disintegrants, flow regulators, plasticizers, wetting agents, dispersants, emulsifiers, solvents, retarding agents, antioxidants and/or propellant gases (cf. H. Sucker et al.: Pharmazeutische Technologie, Thieme-Verlag, Stuttgart, 1978). The pharmaceutical forms obtained in this way normally contain the active substance in an amount of from 1 to 99% by weight.

The following Examples illustrate the invention:

EXAMPLE 1

4-Methyl-5-[3-(1,2,3,6-tetrahydro-4-phenylpyridyl)-propyl]-thiazole-2-one hydrochloride

EXAMPLES 1. 2-Amino-4-methyl-5-[2-(4-phenylpiperidinyl)ethylthio]thiazole hydrochloride 9.65 g of 2-amino-5-bromo-4-methylthiazole, 11.1 g of 2-(4-phenyl-1-piperidinyl)ethyl mercaptan and 20.7 g of potassium carbonate in 50 ml of dimethylformamide were stirred at 80° C. for 30 minutes. The mixture was poured into ice-water and extracted with methylene chloride, and the organic phase was washed with water, dried and concentrated. The residue was purified by chromatography (SiO$_2$; CH$_2$Cl$_2$, CH$_3$OH (0–20%)). The hydrochloride was prepared by dissolving the free base in methanol and adding ethereal HCl.

Yield: 4.8 g (26%); melting point: 205°–210° C.

The following were prepared in a similar way:

2. 2-Amino-5-[2-(1,2,3,6-tetrahydro-4-phenylpyridinyl)-ethylthio]-4-methylthiazole hydrochloride Yield: 17%; melting point: 204°–206° C.
3. 2-Amino-4-methyl-5-[2-(4-phenylpiperazinyl)ethylthio]thiazole hydrochloride Yield: 20%; melting point: 235°–237° C.
4. 2-Amino-5-[2-(4-phenylpiperazinyl)ethylthio]-thiazole hydrochloride Yield: 15%; melting point: from 55°C. (decomposition)
5. 2-Amino-4-methyl-5-[2-(N-phenethyl-N-propylamino)-ethylthio]thiazole hydrochloride Yield: 25%; melting point: 104° C.
6. 2-Amino-4-methyl-5-[2-(4-pyridin-2-ylpiperazinyl)ethylthio]thiazole tartrate Yield: 20%; melting point: 122°–123° C.
7. 2-Amino-4-methyl-5-[3-(N-phenethyl-N-propylamino)propylthio]thiazole tartrate Yield: 31%; melting point: 118°–120° C.

Examples of pharmaceutical forms:

A) Tablets of the following composition are made in a tableting machine in a conventional way.
   40 mg of substance of Example 1
   120 mg of corn starch
   13.5 mg of gelatin
   45 mg of lactose
   2.25 mg of Aerosil ® (chemically pure silica in submicroscopically fine distribution)
   6.75 mg of potato starch (as 6% paste)

B)
   20 mg of substance of Example 4
   60 mg of core composition
   60 mg of coating composition The core composition comprises 9 parts of corn starch, 3 parts of lactose and 1 part of 60:40 vinylpyrolidone/vinyl acetate copolymer. The coating composition comprises 5 parts of sucrose, 2 parts of corn starch, 2 parts of calcium carbonate and 1 part of talc. The coated tablets produced in this way are subsequently provided with an enteric coating.

c) 10 g of substance of Example 2 are dissolved in 5000 ml of water with the addition of NaCl and adjusted to pH 6.0 with 0.1N NaOH to produce a solution isotonic with blood. 1 ml portions of this solution are introduced into ampoules and sterilized.

We claim:

1. An aminoalkyl-substituted 5-mercaptothiazole of the formula I

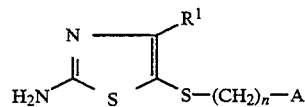

where
R$^1$ is H, C$_1$–C$_5$-alkyl, phenyl which is unsubstituted or substituted by halogen, C$_1$–C$_5$-alkyl or C$_1$–C$_5$-alkoxy, or is thienyl,
n is an integer from 2 to 6,
A is NR$^2$R$^3$ where R$^2$ and R$^3$, which can be identical or different, are each hydrogen, C$_1$–C$_5$-alkyl, which is unsubstituted or substituted by phenyl or thienyl, or is

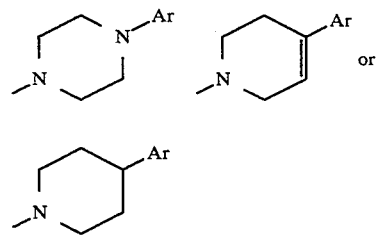

where Ar is phenyl which is unsubstituted or mono-substituted by C$_1$–C$_5$-alkyl, C$_1$–C$_5$-alkoxy, amino, halogen, nitro, hydroxyl, trifluoromethyl or cyano, or is pyridyl, pyrimidinyl or thienyl, and its salts with physiologically tolerated acids.

2. An aminoalkyl-substituted 5-mercaptothiazole of the formula I as defined in claim 1, which is 4-methyl-5-[3-(1,2,3,6-tetrahydro-4-phenylpyridyl)-propyl]-thiazolin-2-onehydrochloride.

3. An aminoalkyl-substituted 5-mercaptothiazole of the formula I as defined in claim 1, which is 2-amino-4-methyl-5-[2-(4-phenylpiperidinyl)ethylthio]thiazole hydrochloride.

4. An aminoalkyl-substituted 5-mercaptothiazole of the formula I as defined in claim 1, which is 2-amino-5-[2-(1,2,3,6-tetrahydro-4-phenylpyridinyl)-ethylthio]-4-methylthiazole hydrochloride.

5. An aminoalkyl-substituted 5-mercaptothiazole of the formula I as defined in claim 1, which is 2-amino-4-methyl-5-[2-(4-phenylpiperazinyl)ethylthio]thiazole hydrochloride.

6. An aminoalkyl-substituted 5-mercaptothiazole of the formula I as defined in claim 1, which is 2-amino-5-

[2-(4-phenylpiperazinyl)ethylthio]thiazole hydrochloride.

7. An aminoalkyl-substituted 5-mercaptothiazole of formula I as defined in claim 1, which is 2-amino-4-methyl-5-[2-N-phenethyl-N-propylamino)-ethylthio]-thiazole hydrochloride.

8. An aminoalkyl-substituted 5-mercaptothiazole of the formula I as defined in claim 1, which is 2-amino-4-methyl-5-[2-(4-pyridin-2-ylpiperazinyl)-ethylthio]-thiazole tartrate.

9. An aminoalkyl-substituted 5-mercaptothiazole of the formula I as defined in claim 1, which is 2-amino-4-methyl-5-[3-(N-phenethyl-N-propylamino)-propylthio]thiazole tartrate.

10. A method for controlling high blood pressure, Parkinson's disease and schizophrenia, which comprises administering to a patient in need thereof an effective amount of the aminoalkyl-substituted 5-mercaptothiazole of the formula I as defined in claim 1.

11. A pharmaceutical composition for treating high blood pressure, Parkinson's disease and schizophrenia, which comprises the aminoalkyl-substituted 5-mercaptothiazole of the formula I as defined in claim 1 and pharmaceutically acceptable carriers and/or additives.

* * * * *